US008277048B2

(12) United States Patent
Artsyukhovich et al.

(10) Patent No.: US 8,277,048 B2
(45) Date of Patent: Oct. 2, 2012

(54) OPHTHALMIC ENDOILLUMINATION USING FIBER GENERATED LIGHT

(75) Inventors: Alexander N. Artsyukhovich, Irvine, CA (US); Mark Buczek, Oceanside, CA (US); Bruno Dacquay, Irvine, CA (US); Michael J. Yadlowsky, Irvine, CA (US)

(73) Assignee: Alcon Research, Ltd., Fort Worth, TX (US)

( * ) Notice: Subject to any disclaimer, the term of this patent is extended or adjusted under 35 U.S.C. 154(b) by 382 days.

(21) Appl. No.: 12/687,190

(22) Filed: Jan. 14, 2010

(65) Prior Publication Data

US 2010/0182569 A1 Jul. 22, 2010

Related U.S. Application Data

(60) Provisional application No. 61/146,173, filed on Jan. 21, 2009.

(51) Int. Cl.
*A61B 3/10* (2006.01)

(52) U.S. Cl. ............... 351/221; 351/213; 351/214

(58) Field of Classification Search ............ 351/213, 351/214, 221; 362/551, 574; 606/4, 15–17
See application file for complete search history.

(56) References Cited

U.S. PATENT DOCUMENTS

| 4,227,939 A | 10/1980 | Zewail et al. | |
|---|---|---|---|
| 4,852,567 A * | 8/1989 | Sinofsky | 606/3 |
| 5,688,264 A * | 11/1997 | Ren et al. | 606/15 |
| 6,510,995 B2 | 1/2003 | Muthu et al. | |
| 6,540,670 B1 | 4/2003 | Hirata et al. | |
| 6,850,673 B2 | 2/2005 | Johnston, II et al. | |
| 2005/0251119 A1 | 11/2005 | Eaton et al. | |
| 2009/0059359 A1 * | 3/2009 | Nahm et al. | 359/368 |

FOREIGN PATENT DOCUMENTS

| EP | 1522290 | 4/2005 |
|---|---|---|
| EP | 1734302 | 12/2006 |
| EP | 1867272 | 12/2007 |
| WO | WO 91/15793 | 10/1991 |
| WO | WO 2008/106590 | 9/2008 |

OTHER PUBLICATIONS

International Search Report for PCT/US2010/021001, Publication No. WO2010/085414, 5 pages.
Written Opinion of the International Searching Authority, International Application No. PCT/US2010/021001, 7 pages.

* cited by examiner

*Primary Examiner* — Ricky Mack
*Assistant Examiner* — Mahidere Sahle
(74) *Attorney, Agent, or Firm* — Keiko Ichiye

(57) ABSTRACT

In one aspect of the invention, an ophthalmic endoilluminator includes at least one pump light source and a scintillator fiber optically coupled to the pump light source. The scintillator fiber receives an output of the pump light source and produces light in a different wavelength range than the output of the pump light source. An optical coupling element couples the light to an optical fiber, which conducts the light into an eye.

30 Claims, 6 Drawing Sheets

OPHTHALMIC ENDOILLUMINATION USING FIBER GENERATED LIGHT

RELATED APPLICATIONS

This application claims priority to U.S. provisional application Ser. No. 61/146,173 filed on Jan. 21, 2009, the contents which are incorporated herein by reference.

TECHNICAL FIELD OF THE INVENTION

The present invention relates to an illuminator for use in ophthalmic surgery and more particularly to an ophthalmic endoilluminator to produce a light suitable for illuminating the inside of an eye.

BACKGROUND OF THE INVENTION

Anatomically, the eye is divided into two distinct parts—the anterior segment and the posterior segment. The anterior segment includes the lens and extends from the outermost layer of the cornea (the corneal endothelium) to the posterior of the lens capsule. The posterior segment includes the portion of the eye behind the lens capsule. The posterior segment extends from the anterior hyaloid face to the retina, with which the posterior hyaloid face of the vitreous body is in direct contact. The posterior segment is much larger than the anterior segment.

The posterior segment includes the vitreous body—a clear, colorless, gel-like substance. It makes up approximately two-thirds of the eye's volume, giving it form and shape before birth. It is composed of 1% collagen and sodium hyaluronate and 99% water. The anterior boundary of the vitreous body is the anterior hyaloid face, which touches the posterior capsule of the lens, while the posterior hyaloid face forms its posterior boundary, and is in contact with the retina. The vitreous body is not free-flowing like the aqueous humor and has normal anatomic attachment sites. One of these sites is the vitreous base, which is a 3-4 mm wide band that overlies the ora serrata. The optic nerve head, macula lutea, and vascular arcade are also sites of attachment. The vitreous body's major functions are to hold the retina in place, maintain the integrity and shape of the globe, absorb shock due to movement, and to give support for the lens posteriorly. In contrast to aqueous humor, the vitreous body is not continuously replaced. The vitreous body becomes more fluid with age in a process known as syneresis. Syneresis results in shrinkage of the vitreous body, which can exert pressure or traction on its normal attachment sites. If enough traction is applied, the vitreous body may pull itself from its retinal attachment and create a retinal tear or hole.

Various surgical procedures, called vitreo-retinal procedures, are commonly performed in the posterior segment of the eye. Vitreo-retinal procedures are appropriate to treat many serious conditions of the posterior segment. Vitreo-retinal procedures treat conditions such as age-related macular degeneration (AMD), diabetic retinopathy and diabetic vitreous hemorrhage, macular hole, retinal detachment, epiretinal membrane, CMV retinitis, and many other ophthalmic conditions.

A surgeon performs vitreo-retinal procedures with a microscope and special lenses designed to provide a clear image of the posterior segment. Several tiny incisions just a millimeter or so in length are made on the sclera at the pars plana. The surgeon inserts microsurgical instruments through the incisions such as a fiber optic light source to illuminate inside the eye, an infusion line to maintain the eye's shape during surgery, and instruments to cut and remove the vitreous body.

During such surgical procedures, proper illumination of the inside of the eye is important. Typically, a thin optical fiber is inserted into the eye to provide the illumination. A light source, such as a metal halide lamp, a halogen lamp, a xenon lamp, or a mercury vapor lamp, is often used to produce the light carried by the optical fiber into the eye. The light passes through several optical elements (typically lenses, mirrors, and attenuators) and is emitted to the optical fiber that carries the light into the eye. The quality of this light is dependent on several factors including the types of optical elements selected.

SUMMARY OF THE INVENTION

In one aspect of the invention, an ophthalmic endoilluminator includes at least one pump light source and a scintillator fiber optically coupled to the pump light source. The scintillator fiber receives an output of the pump light source and produces light in a different wavelength range than the output of the pump light source. An optical coupling element couples the light to an optical fiber, which conducts the light into an eye.

In another aspect of the invention, an ophthalmic endoilluminator comprises at least one pump light source and a plurality of scintillator fibers optically coupled to the at least one pump light source. Each of the plurality of scintillator fibers is operable to receive an output of the at least one pump light source and to produce a plurality of optical outputs. Each of the optical outputs of the fluorescent fibers is in a respective wavelength range different from a wavelength range of the at least one pump source. The ophthalmic endoilluminator further includes an optical combining element operable to combine the plurality of optical outputs in order to produce a combined optical output, an optical coupling element operable to receive the combined optical output, and an optical fiber optically coupled to the optical coupling element. The optical fiber is operable to conduct the combined optical output into an eye.

In still another aspect of the invention, a method comprises generating a first output from at least one pump light source and optically coupling the first output to at least one optical fiber to produce at least one optical output having a different spectral output from that of the first output. The method further comprises optically coupling the at least one optical output to an ophthalmic endoilluminator fiber with an optical coupling element, and conducting the optical output with the ophthalmic endoilluminator fiber to illuminate an interior region of an eye.

In yet another aspect of the invention, an ophthalmic endoilluminator comprises at least one pump light source and at least one fluorescent fiber optically coupled to the at least one pump source. The at least one fluorescent fiber receives an output of the at least one pump source. Regions of the at least one fluorescent fiber are doped with Red, Green or Blue (RGB) organic dyes. The at least one fluorescent fiber is operable to produce RGB optical outputs from the output of the at least one pump source. The ophthalmic endoilluminator further comprises an optical combining element operable to combine the plurality of optical outputs and produce light, an optical coupling element operable to receive the light, and an optical fiber optically coupled to the optical coupling element. The optical fiber is operable to conduct the light into an eye.

Another aspect of the invention provides an ophthalmic endoilluminator comprising at least one pump light source and a scintillator fiber optically coupled to the at least one pump light source. The scintillator fiber comprising a scintillator device at a distal end of the scintillator fiber adapted for positioning within an eye. The scintillator fiber carries an optical output of the at least one pump light source to the scintillator device, and the scintillator device is operable to receive the optical output and to produce light in a different wavelength range than the optical output of the at least one pump light source.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein.

DESCRIPTION OF THE INVENTION

Preferred embodiments of the present invention are illustrated in the Figures, like numerals being used to refer to like and corresponding parts of the various drawings.

Embodiments of the present invention provide an ophthalmic endoilluminator is that includes one or more pump light sources, an optical fiber, such as the scintillator fiber or fluorescent fiber. The optical fiber couples to the pump light sources to receive an output of the pump light sources and produce an optical output, such as white light in certain embodiments of the scintillator fiber having a white phosphor in either the core or cladding or red-green-blue (RGB) outputs in the case of certain embodiments using dyed fluorescent fibers. An optical coupling element coupled to the optical fiber receives the optical output and provides the optical output to an endoilluminator fiber which conducts the light into an interior region of the eye.

Figure 1:
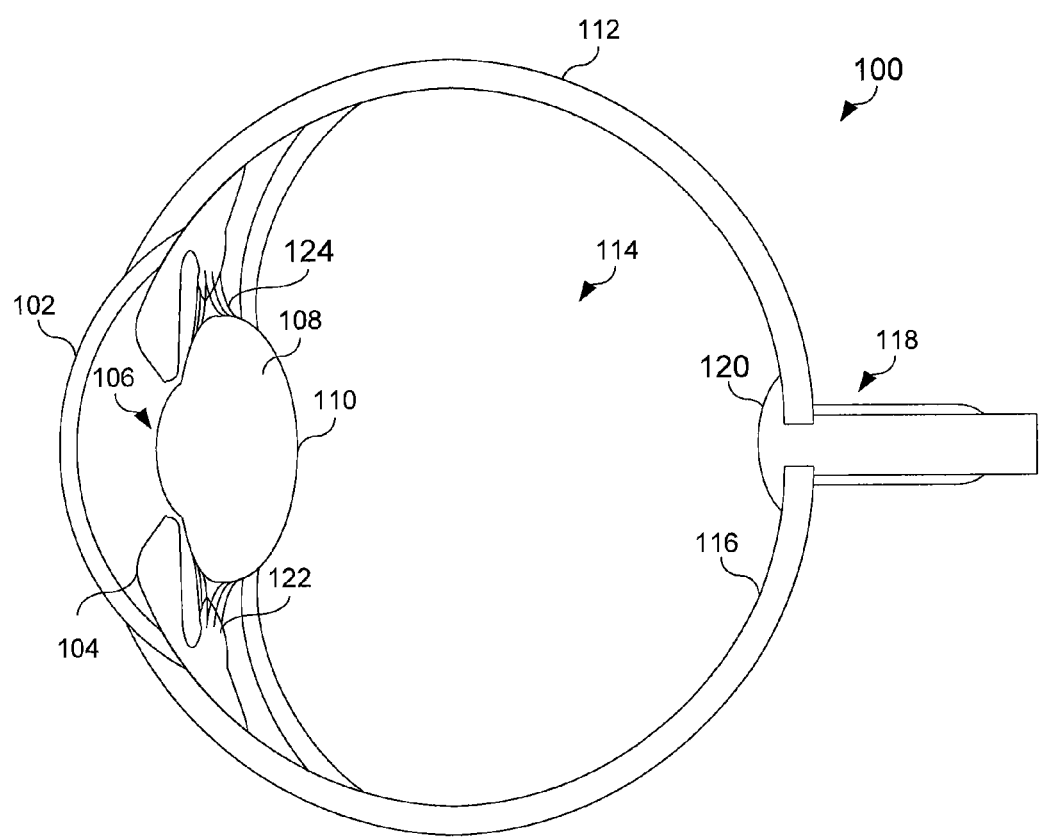
FIG. 1 illustrates the anatomy of the eye in which an ophthalmic endoilluminator in accordance with embodiments of the present invention may be placed.

FIG. 1 illustrates the anatomy of the eye into which the improved design for ocular implant provided by the present invention may be placed. Eye 100 includes cornea 102, iris 104, pupil 106, lens 108, lens capsule 110, zonules, ciliary body 120, sclera 112, vitreous gel 114, retina 116, macula, and optic nerve 120. Cornea 102 is a clear, dome-shaped structure on the surface of the eye acts as a window, letting light into the eye. Iris 104 is the colored part of the eye, called the iris, is a muscle surrounding the pupil that relaxes and contracts to control the amount of light entering the eye. Pupil 106 is the round, central opening of the iris. Lens 108 is the structure inside the eye that helps to focus light on the retina. Lens capsule 110 is an elastic bag that envelops the lens, helping to control lens shape when the eye focuses on objects at different distances. Zonules are slender ligaments that attach the lens capsule to the inside of the eye, holding the lens in place. The ciliary body is the muscular area attached to the lens that contracts and relaxes to control the size of the lens for focusing. Sclera 112 is the tough, outermost layer of the eye that maintains the shape of the eye. Vitreous gel 114 is the large, gel-filled section that is located towards the back of the eyeball, and which helps to maintain the curvature of the eye. Retina 116 is a light-sensitive nerve layer in the back of the eye that receives light and converts it into signals to send to the brain. The macula is the area in the back of the eye that contains receptors for seeing fine detail. Optic nerve 118 connects and transmits signals from the eye to the brain.

Ciliary body 122 lies just behind the iris 104. Attached to the ciliary body 122 are tiny fiber "guide wires" called zonules 124. Lens 108 is suspended inside the eye by the zonular fibers 124. Nourishment for the ciliary body 122 comes from blood vessels which also supply the iris 104. One function of ciliary body 122 is to control accommodation by changing the shape of the lens 108. When the ciliary body 122 contracts, the zonules 124 relax. This allows the lens 108 to thicken, increasing the eye's ability to focus up close. When looking at a distant object, ciliary body 122 relaxes, causing the zonules 124 to contract. The lens 108 then becomes thinner, adjusting the eye's focus for distance vision.

Figure 2:
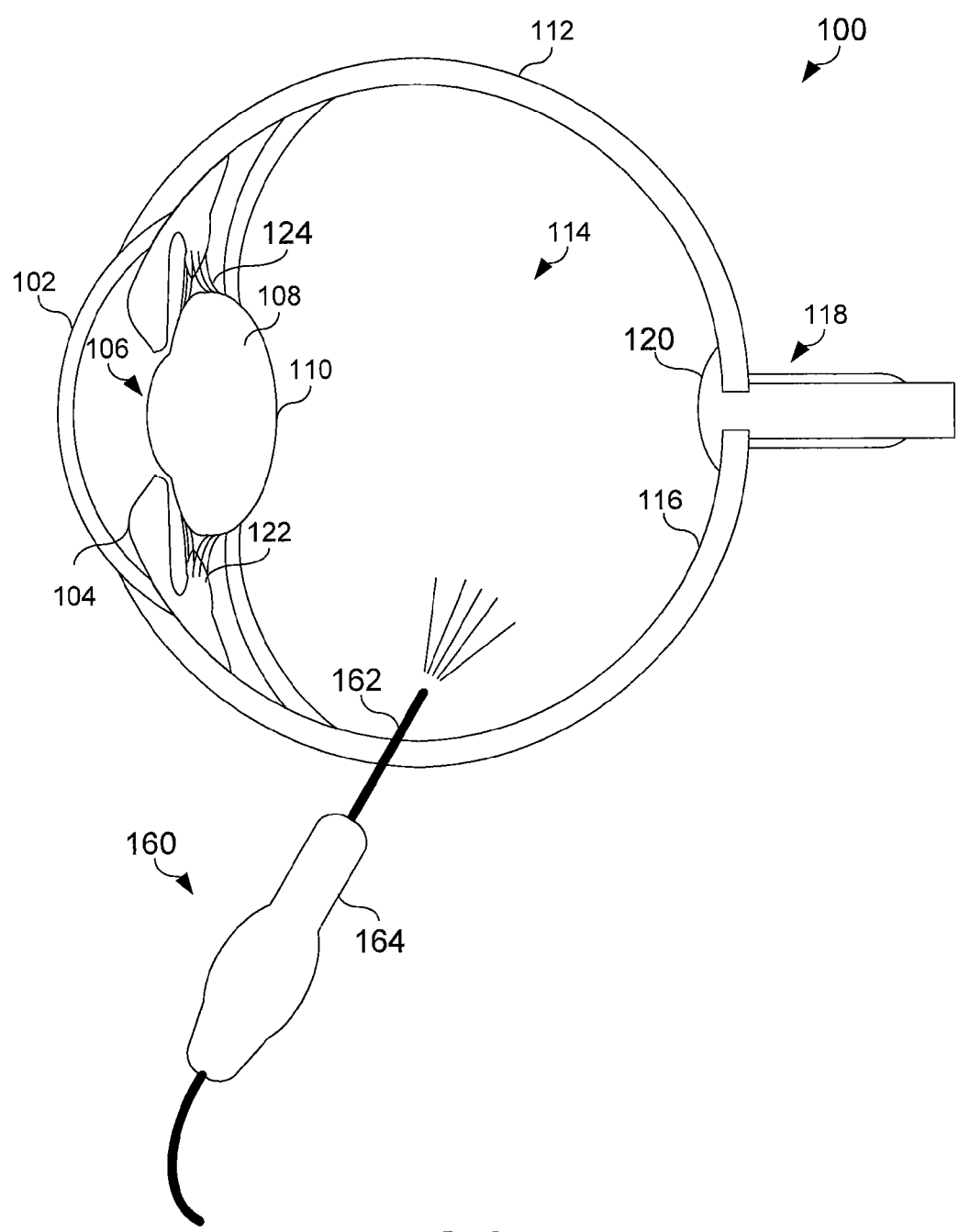
FIG. 2 illustrates an ophthalmic endoilluminator illuminating the interior of the eye in accordance with embodiments of the present invention.

FIG. 2 is a cross sectional view of an ophthalmic endoilluminator 160, which may be an endoilluminator according to various embodiments of the present invention, located in an eye. FIG. 2 depicts handpiece 164 with probe 162 in use. Probe 162 is inserted into eye 100 through an incision in the pars plana region. Probe 162 illuminates the inside or vitreous region 114 of eye 100. In this configuration, probe 162 can be used to illuminate the inside or vitreous region 114 during vitreo-retinal surgery.

Ophthalmic endoilluminators have been previously based either on halogen tungsten lamps or high pressure arc lamps (metal-halides, Xe). The advantages of arc lamps are small emitting area (<1 mm), color temperature close to daylight, and longer life than in halogen lamps—400 hours vs. 50 hours. The disadvantage of arc lamps is high cost, decline in power, complexity of the systems and the need to exchange lamps several times over the life of the system.

LED based illuminators may provide considerably lower cost and complexity, and characteristic life times of 50,000 to 100,000 hours that would allow operating ophthalmic fiber illuminator for entire life of the instrument with very little drop in output and without a need of exchanging LEDs. A typical white LED may include ultra violet (UV)/violet/blue LED exciting a white phosphor cap that emits white light. Because of the size of the phosphor cap required to produce significant amounts of white light, conventional white LEDs are spatially extended sources of illumination with high numerical aperture (NA) as compared to optical fibers used in ophthalmic surgery. Thus conventional white LEDs are not generally suited well for coupling into such optical fibers. Available pigtailed fiber illuminators based on white LEDs use fiber butted against LED phosphor. Only a small fraction of light can be coupled into low numerical aperture and small diameter optical fiber. Therefore available pigtailed white LED sources deliver low levels of light.

Unlike conventional illuminators, various embodiments of the present invention generate optical signals such as (but not limited to) white light, RGB optical signals, yellow and blue optical signals, and turquoise and red optical signals, etc., from the output of a pump source directly inside optical fiber. For example there is possibility of using green 532 nm laser as pump source and yellow dye to convert the 532 nm optical signal into yellow illumination at the end of fiber illuminator. Rather than illuminate a large phosphor area with a UV/violet/blue LED to produce light, as conventional white LEDs do, and then struggle to collect light of such high-NA, extended light source into a fiber, various embodiments of the present invention illuminate luminescent fiber (core or cladding) with UV/violet/blue light. UV/violet/blue LEDs or similar monochromatic LEDs may typically be made with a much smaller NA and greater intensity than white LEDs, and they may be formed in strips or other convenient shapes so that they can more easily be coupled to the optical fibers used in ophthalmic surgery. Although luminescence will occur in all directions, a significant portion of re-emitted white light will fall inside the fiber NA and will be trapped inside the fiber. This can concentrate the resulting light so that the end of the illuminator fiber delivers a much higher level of illumination per area than when a conventional white LED is coupled to the fiber. To increase probability of UV/violet/blue light absorption the system could be placed inside a reflective cavity, an integrating sphere or a light pipe. Any of these approaches could considerably increase the number of UV ray passes and increase pumping efficiency.

The terms "scintillator fiber" and "scintillator device" are used herein to refer to any structure formed from a material capable of converting pumping radiation into another range of the electro-magnetic spectrum, including but not limited to the conversion of high energy particle rays, x-rays and UV to lower energy photons. Any suitable type of scintillator for producing illumination may be employed according to various embodiments of the present invention. Conversion efficiency is a significant benefit of particular embodiments of the present invention, and the luminescence process utilized for conversion could be either based on slow emission (phosphorescence) or fast emission (fluorescence), depending on which materials are used. Where description is made below with respect to particular types of scintillator fibers or devices, e.g., fluorescent fibers, it should be understood that any suitable type of scintillator fiber or device may be used in its place.

Embodiments of the present invention use a scintillator fiber with a luminescent core or cladding and a pump light source, such as a UV or Blue light source, along with an optional reflecting system to allow for multiple reflection of pumping radiation. Such a scintillator fiber may be used, for example, to convert UV/violet/blue light illumination from a pump light source into broadband or white light through luminescence. Part of re-emitted white light propagates through scintillator fiber and can be either coupled to regular optical fiber or delivered to an illumination device directly. Such a scintillator fiber can also be placed in a UV-reflective integrating sphere or light pipe for pumping. One can also draw on various pumping schemes of lasers for examples of similar techniques for light generation, with the significant difference that the output of the scintillator fiber need not necessarily be coherent.

Embodiments of the present invention may utilize one or more pump light sources, such as LEDs. As is known to one skilled in the art, there are many types of LEDs with different power ratings and light output that can be selected as pump source 302. Alternatively, other pump light sources, such as lasers, could be used. Although particular embodiments are described herein having LEDs used as pump sources, it will be apparent to one skilled in the art that other suitable pump light sources could be used in place of LEDs.

In one example, as will be discussed with reference to FIG. 3, the output of a single pump LED is directed onto a scintillator fiber, which has a doped cladding or core (e.g. with white phosphor). Because light of a particular wavelength generated by the luminescent dopant will be generated in both directions along the fiber, the near/pump end of fiber may be covered with a mirror to reflect all light in the same output direction but to pass the pump wavelength. Both the pump LED and scintillator fiber are placed in this example inside light pipes that allow for multiple passes of the pump light to be absorbed by the scintillator fiber. The distal end of the light pipe is covered with mirror to prevent pumping UV losses. The output of the scintillator fiber may then be easily coupled into a standard ophthalmic endoilluminator through ball lens or other optics.

Figure 3:
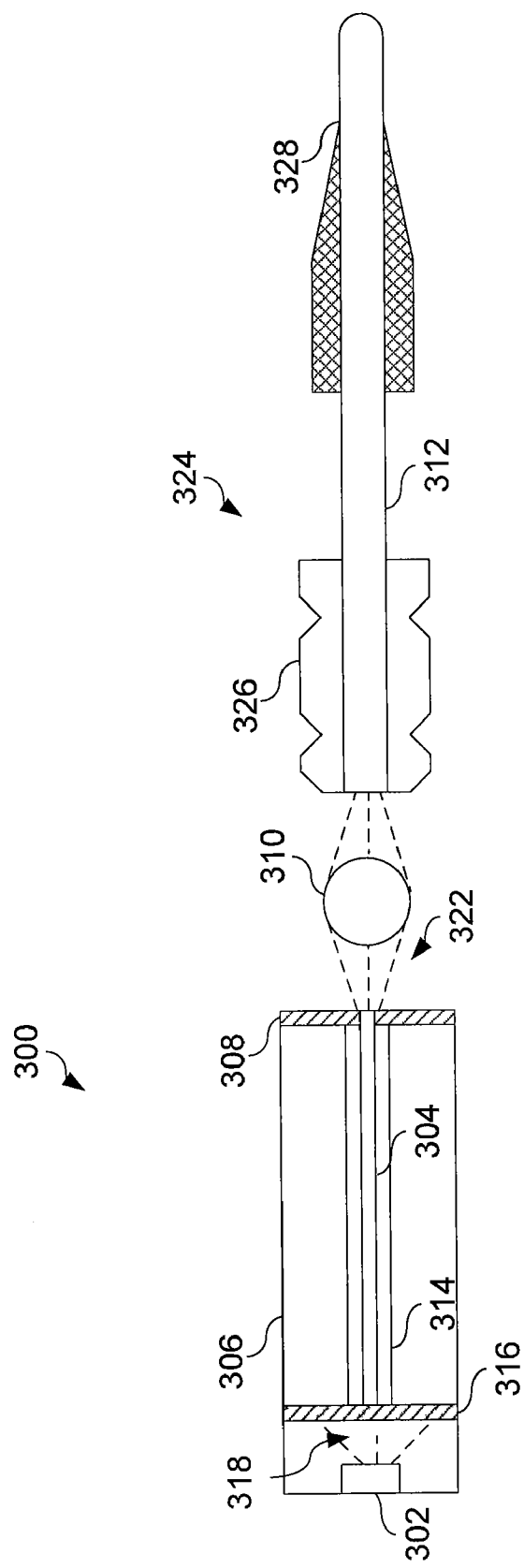
FIG. 3 is a block diagram of an LED pumped ophthalmic endoilluminator using scintillator fibers in accordance with embodiments of the present invention.

FIG. 3 is a cross-sectional diagram of a single pump LED ophthalmic endoilluminator 300 in accordance with embodiments of the present invention. Ophthalmic endoilluminator 300 includes a pump source LED 302, mirrors 308 and 316, a light pipe 306, optical fiber 204, optical coupler 310 and ophthalmic endoilluminator fiber 312. As shown in FIG. 3 the output 318 of single pump LED 302 is directed to scintillator fiber 304.

Scintillator fiber 304 may be cladding- or core-doped with for example a white phosphor material cladding 314. When using white phosphor material cladding, white light will be generated in all directions along fiber 304. As such, the near or pump end of scintillator fiber 304 may be covered with a mirrored or reflective surface 316 operable to reflect all light in a common output direction while still passing the output of pump LED 318 emitted from pump source 302.

Pump LED 302 and scintillator fiber 304 may be placed inside a light pipe 306 that allows for multiple passes of pump light 318 which is absorbed by scintillator fiber 304. Scintillator fiber 304 optically couples to an ophthalmic endoilluminator fiber 312 through a ball lens 310 or other suitable optical system. The core diameter and numerical aperture of scintillator fiber 304 may be chosen such that it is equal to or less than that of the optical fiber 312, which facilitates optically coupling the scintillator fiber 304 to the optical fiber 312 and improves the efficiency of the optical coupling between the two fibers 304 and 312. The resulting optical signal 322 is directed through connector 310 and optical fiber 312 to probe 162 where it illuminates the inside of the eye 100.

Ordinarily, the retina is protected from ultraviolet light by the eye's natural lens, which filters the light that enters the eye. But light from an optical endoilluminator enters the eye without this lens filtration (i.e., aphakically), so it is desirable for the endoilluminator 300 to include filters to reduce the amount of light emitted in wavelengths that can be harmful to optical tissue. Providing light of the proper range of visible light wavelengths while filtering out harmful short and long wavelengths can greatly reduce the risk of damage to the retina through aphakic hazards, including blue light photochemical retinal damage and infrared heating damage, and similar light toxicity hazards. Typically, a light in the range of about 430 to 700 nanometers is preferable for reducing the risks of these hazards. To this end, mirrors 308 and 316 may be included to allow light of a suitable wavelength to be emitted into an eye. Mirror 316 may, for example, be a dichroic reflector that reflects visible wavelength light and only transmits infrared and ultraviolet light to preserve the light intensity in the visible wavelength spectrum while reducing the relative intensity in the infrared and ultraviolet spectrum. Mirror 308 may similarly reflect long wavelength infrared light and short wavelength ultraviolet light while transmitting visible light, so that the light emitted by the endoilluminator 300 into the eye is almost entirely within the visible wavelength range. Other filters and/or dichroic beam splitters may also be employed to produce a light in this suitable wavelength range.

The endoilluminator handpiece 324 that is handled by the ophthalmic surgeon includes an optical coupling 310, optical fiber 312, housing 326, and probe 328. Optical coupling 310 is designed to connect the optical fiber 312 to a main console (not shown) containing the scintillating fiber 304. Optical coupling 310 properly aligns optical fiber 312 with the output of scintillator fiber 304 that is to be transmitted into the eye. Optical fiber 312 is typically a small diameter fiber that may or may not be tapered. Housing 326 is held by the surgeon and allows for the manipulation of probe 328 in the eye. Probe 328 is inserted into the eye and carries optical fiber 312 which terminates at the end of probe 328. Probe 328 thus provides illumination from optical fiber 312 in the eye.

Embodiments of the present invention may also employ one or more scintillator fibers which have been doped with red, green, and blue (RGB) organic dyes. It is typically easier to dope a fiber with these dyes than with a number of materials with broader emission spectra, such as white phosphor. Thus, scintillator fibers using such RGB dyes may be easier to produce. For example three coils of such RGB fibers placed into an integrating sphere and illuminated with UV LEDs will create a strong RGB output, a phenomenon used in organic LEDs (OLEDs) to produce illumination of various colors efficiently. Then the individual RGB outputs may be combined onto a single fiber. This can be done in a multitude of ways such as but not limited to an RGB X prism, a dispersion prism, or a diffraction grading.

Figure 4:
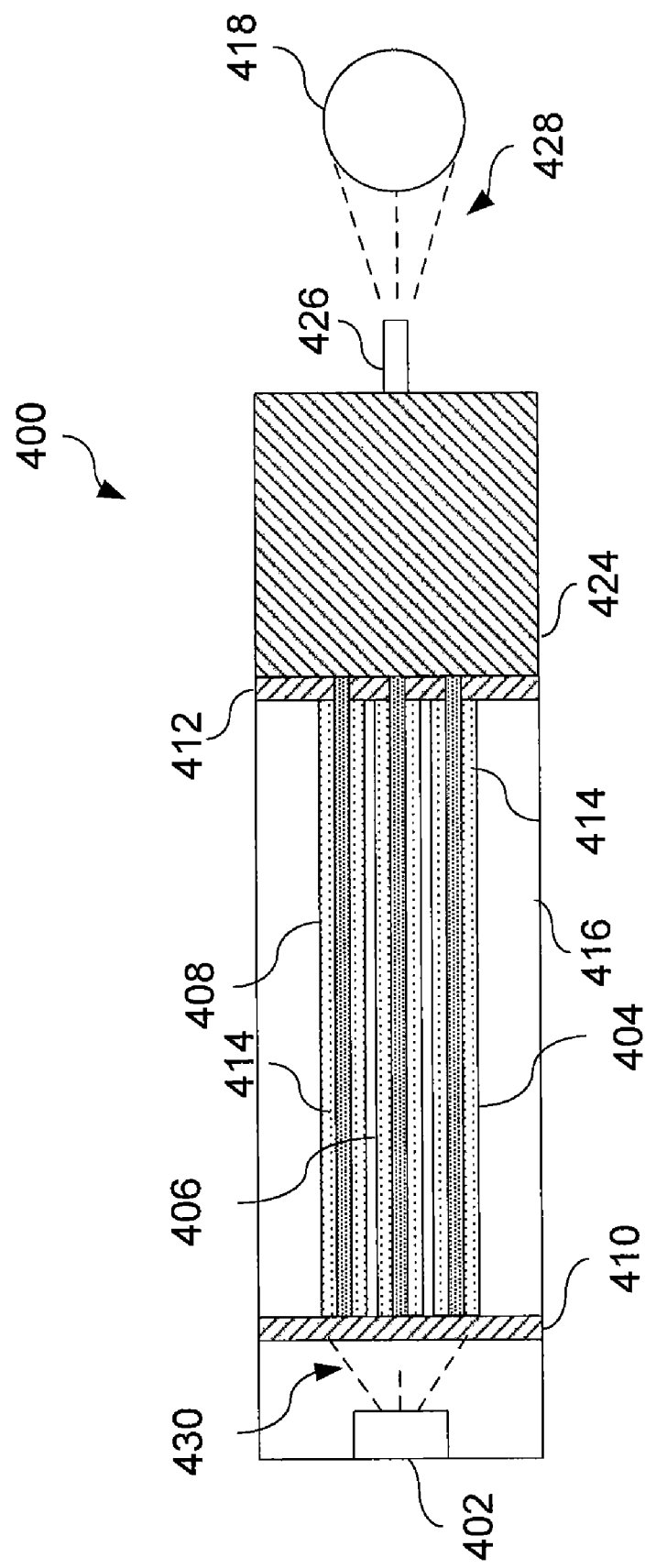
FIG. 4 is a block diagram of an RGB ophthalmic endoilluminator using fluorescent fibers doped with red, green, and blue dyes in accordance with embodiments of the present invention.

FIG. 4 depicts an RGB light source 400 for use with an ophthalmic endoilluminator using fluorescent fibers doped with red, green, and blue dyes in accordance with embodiments of the present invention. The light source 400 of the ophthalmic endoilluminator includes a pumping source 402, RGB fluorescent fibers 404, 406, and 408, mirrors 410 and 412, a phosphor core or cladding 414 on the fluorescent fibers, light pipe 416, optical coupling element 418, and ophthalmic 420 having an optical fiber 422. Pump source 402 generate UV or blue light 430 which is passed to fluorescent fibers 404, 406 and 408. The individual fibers 404, 406, and 408 create an RG and B optical output respectively. At combiner 424 the RGB optical outputs from optical fibers 404, 406, and 408 combine such that the optical outputs are provided to a combined optical fiber 426.

Placing coils of such RGB fibers into an integrating sphere and illuminating the fibers with UV LEDs will create a strong RGB output. Then the RGB output is combined in a single fiber. This can be done in various ways—such as a ball lens, an RGB X-prism, a dispersion prism, or a diffraction grating. Alternatively, as will be discussed with reference to FIG. 5 one can have three (or more) consecutive regions along single fiber doped with 3 (or more) dyes. Self-absorption of RGB emission by other color dye can be limited if the dopants are ordered red, green then blue moving towards the illumination exit. Combined optical fiber 426 passes the RGB or white light output to ophthalmic endoilluminator fiber 312 by optically coupling the output 428 of combined optical fiber 426 to the ophthalmic endoilluminator fiber 422 using an optical coupling such as ball lens 418.

While the use of dye-doped fibers to produce colors is described, the dye doped fibers can also be replaced by capillary fibers filled with dye solutions. More generally, colors can be produced in any suitable manner, such as by production of F-centers or other crystalline defects, variable size quantum dots or nano-pores, using any suitable technique for producing such features, including but not limited to gamma irradiation, selective chemical etching, or nano-deposition. It will be understood by one skilled in the art that these alternative methods may be substituted in the various embodiments of the invention described herein.

Figure 5:
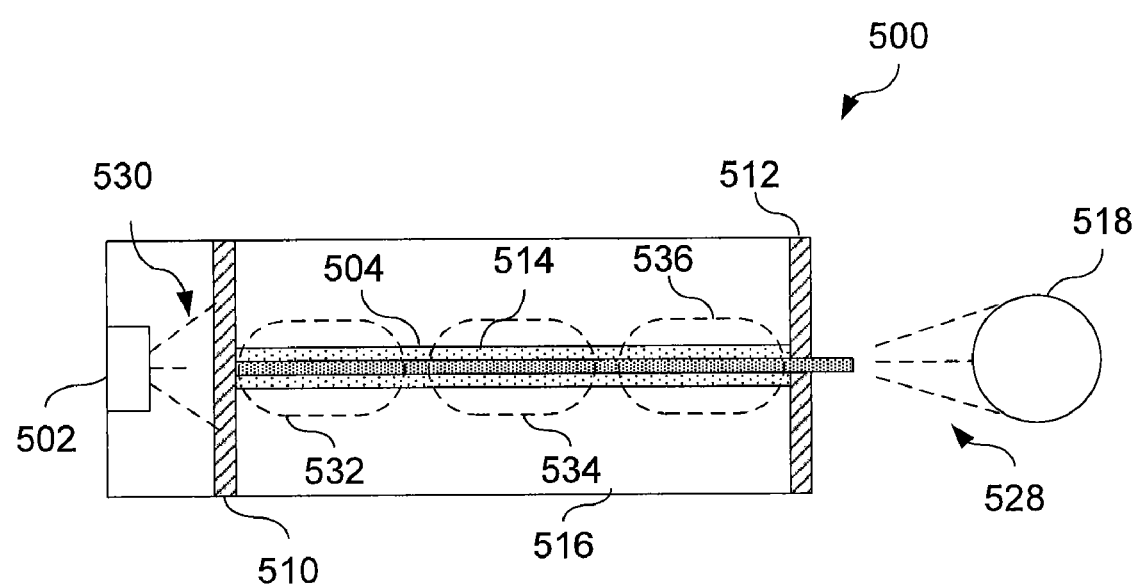
FIG. 5 is a block diagram of an RGB ophthalmic endoilluminator using a fluorescent fiber having different regions doped with red, green, and blue dyes in accordance with embodiments of the present invention.

FIG. 5 depicts another RGB light source 500 for use with an ophthalmic endoilluminator using a single fluorescent fiber doped with red, green, and blue dyes in different regions 532, 534 and 536 in accordance with embodiments of the present invention. The light source 500 of the ophthalmic endoilluminator includes a pump light source 502, RGB fluorescent fibers 504, mirrors 510 and 512, a phosphor core or cladding 514 on the fluorescent fibers, light pipe 516, and optical coupling element 518. Pump light source 502 generates UV or blue light 530 which is passed to fluorescent fibers 504. Fiber 504 creates an RGB optical output that is passed into ophthalmic endoilluminator fiber 312 by optically coupling the output 528 of the optical fiber to the ophthalmic endoilluminator fiber 312 using an optical coupling such as ball lens 518.

In FIG. 5, one optical fiber 504 is used having three or more consecutive regions 532, 534, and 536 that are doped with three or more dyes, respectively. Self-absorption of RGB emission by other color dye can be limited if the dopants are ordered red, green, and then blue moving towards the illumination exit 506. Dye doped fibers can also be replaced by capillary fibers filled with dye solutions.

Another embodiment, which can be used in the configuration depicted in FIG. 2, may transport all UV to the distal end of the fiber without converting it into visible light. The distal end of fiber will then be terminated with a scintillator device—a section of fiber doped with phosphor, a fluorescent or phosphor cap. Thus only UV/Violet/Blue radiation will be coupled into fiber, while the actual conversion of high energy photons into visible light photons will occur at the very tip of the fiber illuminator. Coupling UV light into fiber may be easier, because the source size—an LED stripe—is much smaller (typically hundreds of microns) than a phosphor cup of white LED (typically 1-3 mm). Because UV light may be transmitted into the eye in such an embodiment, it may also be desirable to include an optical filter, such as around the body of the scintillator fiber, in order to prevent UV light from reaching optical tissue.

Figure 6:
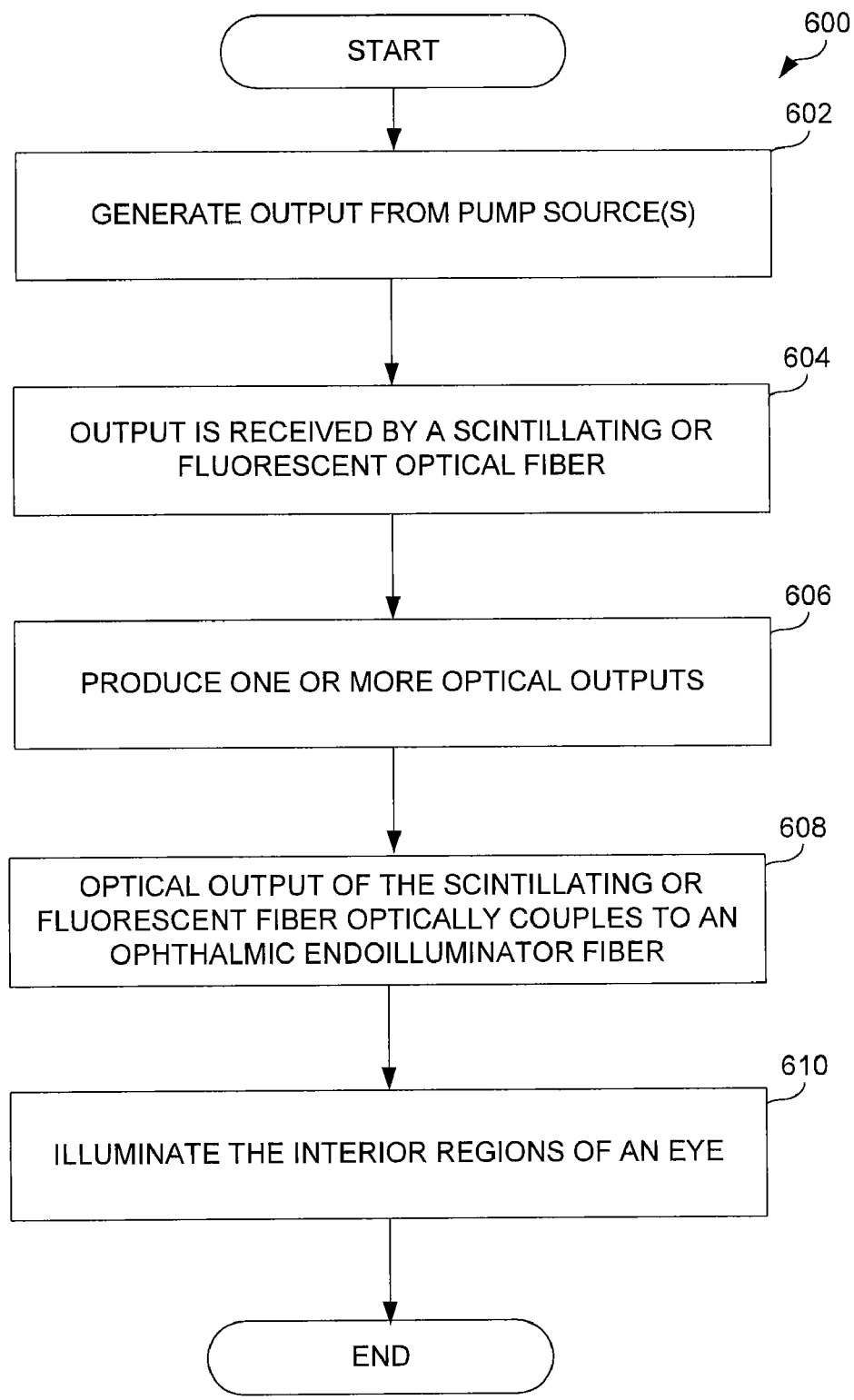
FIG. 6 provides a logic flow diagram associated with a method of illuminating the interior vitreous regions of an eye using an ophthalmic endoilluminator in accordance with embodiments of the present invention.

FIG. 6 provides a logic flow diagram 600 associated with a method of illuminating the interior vitreous regions of an eye using an ophthalmic endoilluminator in accordance with embodiments of the present invention. Operation 600 begins with block 602 where a first output is generated from one or more pump sources. In certain embodiments the pumping source may be an ultraviolet (UV) or blue light source. Various pumping schemes may be used to generate light. These pumping schemes may be similar to those used for pumping laser cavities, with the difference being that the output will not necessarily need to be coherent.

The output is received by a scintillator fiber in block 604. The scintillator fiber will produce one or more optical outputs in block 606. A luminescent core or cladding of the scintillator fiber will allow the pumping source to cause the doped optical fiber that is clad or core doped with a material such as white phosphor to generate a white light in all directions along the fiber. The optical output of the scintillator fiber optically couples to an ophthalmic endoilluminator fiber using an optical coupling element in block 608. This allows the optical fiber of the ophthalmic endoilluminator to conduct white light or other wave lengths generated within the scintillator fiber to illuminate the interior regions of an eye in block 610.

As previously stated the pump source may provide an output to one or more scintillator fibers. These fibers may be doped with red, green or blue organic dyes. This allows the fiber to produce an RGB optical output. The pump source and the scintillator fibers may be placed within a light pipe having mirrors on both ends of the having reflectors to allow for multiple reflections and pumping of the radiation produced by the pumping source. In other embodiments the scintillator fiber may be placed in a UV reflective integrating sphere or a light type for further pumping. The reflective surfaces mirrors at the distal end of the scintillator fibers reflect light within the scintillator fibers to produce light in a common output direction while passing the output of the pump source to the clad or core doped fiber. In block 606, the output of the scintillator fiber is directed to an ophthalmic endoilluminator fiber and may involve combining the optical output from multiple fluorescent fibers. In such an instance an optical combining element such as a ball lens, X-prism, dispersion prism or diffraction grating may be used to combine these optical signals into a single optical signal optically coupled to the optical fiber of the ophthalmic endoilluminator. The core diameter and numerical aperture of the fiber on which the combined outputs of the one or more scintillator fibers is provided is equal to or smaller than that of the ophthalmic endoilluminator fiber.

In summary, embodiments provide an ophthalmic endoilluminator. From the above, it may be appreciated that the present invention provides an improved system for illuminating the inside of the eye. The ophthalmic endoilluminator includes one or more pump light emitting diodes (LEDs), an optical fiber, such as the scintillator fiber or fluorescent fiber. The optical fiber couples to the pump LEDs to receive an output of the LEDs and produce an optical output such as white light in the case of the scintillator fiber having a phosphor core or cladding or RGB outputs in the case of fluorescent fibers. An optical coupling element coupled to the optical fiber receives the optical output and provides the optical output to an endoilluminator fiber which conducts the light into an interior region of the eye.

Very high levels of white light power, automatically coupled into fiber, can be generated using the scintillator fiber technique provided by embodiments of the present invention. For example, 1 m of scintillator fiber illuminated with 10 UV LEDs, could produce 10 Lumens of white light. Because the material of fiber only absorbs in UV and transmits white light with substantial loss, nothing prevents the use of longer fiber segments (e.g. 1 km-long fiber), thus potentially obtaining substantially (e.g. 1000×) more white light already coupled into the fiber. To reduce the number of pump LEDs needed and the length of the scintillator fiber required, the fiber can be coiled, inserted into a reflective cavity, integrating sphere or light pipe. The pump LEDs may then be positioned in order to efficiently couple their output into the scintillator fiber. Also, similar to the case of laser pumping, the amount of dopant used in particular embodiments of the present invention can also be adjusted appropriately to generate more light. For longitudinal pumping of scintillator fiber with a UV laser, for example, a lower doping concentration could be used, with the UV laser being coupled into the scintillator fiber.

The present invention is illustrated herein by example, and various modifications may be made by a person of ordinary skill in the art. Although the present invention is described in detail, it should be understood that various changes, substitutions and alterations can be made hereto without departing from the scope of the invention as claimed.

What is claimed is:

1. An ophthalmic endoilluminator comprising:
   at least one pump light source;
   a scintillator fiber optically coupled to the at least one pump light source, the scintillator fiber operable to receive an output of the at least one pump light source and produce light in a different wavelength range than the output of the at least one pump light source;
   an optical coupling element optically coupled to the scintillator fiber, the optical coupling element operable to receive the light from the scintillator fiber; and
   an optical fiber optically coupled to the optical coupling element, the optical fiber operable to conduct the light into an eye.

2. The ophthalmic endoilluminator of claim 1, wherein a light pipe houses both the at least one pump light source and the scintillator fiber.

3. The ophthalmic endoilluminator of claim 1, further comprising a mirror at a distal end of the scintillator fiber, the mirror operable to reflect light in at least part of the different wavelength range and pass the output of the at least one pump light source.

4. The ophthalmic endoilluminator of claim 1, wherein the scintillator fiber comprises a luminescent core or cladding, the luminescent core or cladding operable to produce the light in the different wavelength range.

5. The ophthalmic endoilluminator of claim 4, wherein the luminescent core or cladding comprises white phosphor.

6. The ophthalmic endoilluminator of claim 1, wherein the optical coupling element comprises a ball lens.

7. The ophthalmic endoilluminator of claim 1, wherein the core diameter and numerical aperture of the scintillator fiber are both either equal to or smaller than that of the optical fiber.

8. The ophthalmic endoilluminator of claim 1, wherein the pump light source comprises a UV or Blue light LED.

9. An ophthalmic endoilluminator comprising:
   at least one pump light source;
   a plurality of scintillator fibers optically coupled to the at least one pump light source, each of the plurality of scintillator fibers operable to receive an output of the at least one pump light source and to produce a plurality of optical outputs, each of the optical outputs of the scintillator fibers in a respective wavelength range different from a wavelength range of the at least one pump source;
   an optical combining element operable to combine the plurality of optical outputs in order to produce a combined optical output;
   an optical coupling element operable to receive the combined optical output; and
   an optical fiber optically coupled to the optical coupling element, the optical fiber operable to conduct the combined optical output into an eye.

10. The ophthalmic endoilluminator of claim 1, wherein a light pipe houses both the at least one pump light source and the plurality of scintillator fibers.

11. The ophthalmic endoilluminator of claim 1, further comprising a mirror at a distal end of the plurality of scintillator fibers, the mirror operable to reflect light and pass the output of the at least one pump light source.

12. The ophthalmic endoilluminator of claim 1, wherein the optical combining element comprises at least one optical combining element selected from the group consisting of:
   an X-prism;
   a dispersion prism; and
   a diffraction grating.

13. The ophthalmic endoilluminator of claim 4, wherein the plurality of fluorescent fibers comprise fluorescent fibers doped with Red, Green and Blue (RGB) organic dyes, the plurality of fluorescent fibers operable to produce RGB optical outputs.

14. The ophthalmic endoilluminator of claim 1, wherein the optical coupling element comprises a ball lens.

15. The ophthalmic endoilluminator of claim 1, wherein the core diameter and numerical aperture of the scintillator fiber are equal or smaller than that of the optical fiber.

16. The ophthalmic endoilluminator of claim 1, wherein the pump source comprises a UV or Blue light pump source.

17. A method comprising:
generating a first output from at least one pump light source;
optically coupling the first output to at least one optical fiber to produce at least one optical output having a different spectral output from that of the first output, wherein the at least one optical fiber comprises a fluorescent fiber;
optically coupling the at least one optical output to an ophthalmic endoilluminator fiber with an optical coupling element; and
conducting the optical output with the ophthalmic endoilluminator fiber to illuminate an interior region of an eye.

18. The method of claim 17, wherein the at least one optical fiber comprises a fluorescent fiber doped with at least two different organic dyes, the organic dyes operable to produce optical outputs of different wavelengths such that the optical outputs produce white light when combined.

19. The method of claim 17, further comprising housing the at least one pump source and the at least one optical fiber within a light pipe.

20. The method of claim 17, further comprising:
reflecting light within the at least one optical fiber to produce light in a same output direction; and
passing the output of the at least one pump source to the at least one optical fiber.

21. The method of claim 17, wherein the optical coupling element comprises at least one optical combining element selected from the group consisting of:
a ball lens;
an X-prism;
a dispersion prism; and
a diffraction grating.

22. The method of claim 17, wherein the core diameter and numerical aperture of the at least one optical fiber are equal or smaller than that of the ophthalmic endoilluminator fiber.

23. The method of claim 17, wherein the pump source comprises a UV or Blue light pump source.

24. An ophthalmic endoilluminator comprising:
at least one pump light source;
at least one fluorescent fiber optically coupled to the at least one pump source, wherein:
the at least one fluorescent fiber receives an output of the at least one pump source;
regions of the at least one fluorescent fiber are doped with Red, Green or Blue (RGB) organic dyes, the at least one fluorescent fiber operable to produce RGB optical outputs from the output of the at least one pump source;
an optical combining element operable to combine the plurality of optical outputs and produce light;
an optical coupling element operable to receive the light; and
an optical fiber optically coupled to the optical coupling element, the optical fiber operable to conduct the light into an eye.

25. An ophthalmic endoilluminator comprising:
at least one pump light source;
a scintillator fiber optically coupled to the at least one pump light source, the scintillator fiber comprising a scintillator device at a distal end of the scintillator fiber adapted for positioning within an eye, wherein:
the scintillator fiber carries an optical output of the at least one pump light source to the scintillator device; and
the scintillator device is operable to receive the optical output and to produce light in a different wavelength range than the optical output of the at least one pump light source.

26. The ophthalmic endoilluminator of claim 25, wherein the pump light source comprises a UV or Blue light LED.

27. The ophthalmic endoilluminator of claim 25, further comprising an optical filter disposed around the scintillator fiber and configured to filter out light in the wavelength range of the optical output of the at least one pump light source.

28. The ophthalmic endoilluminator of claim 25, wherein the scintillator device comprises a fluorescent material.

29. The ophthalmic endoilluminator of claim 25, wherein the scintillator device comprises a phosphorescent material.

30. The method of claim 17, wherein the at least one pump light source is an LED light source.

* * * * *